United States Patent [19]

Anawis et al.

[11] Patent Number: 5,091,318
[45] Date of Patent: Feb. 25, 1992

[54] BINDING OF ALLERGENS TO A SOLID PHASE

[75] Inventors: Mark A. Anawis, Grayslake; Roger E. Lindberg, Libertyville, both of Ill.

[73] Assignee: Abbott Laboratories, Abbott Park, Ill.

[21] Appl. No.: 509,255

[22] Filed: Apr. 13, 1990

[51] Int. Cl.⁵ .................................. G01N 33/563
[52] U.S. Cl. ............................. 436/513; 436/825; 436/826; 436/530; 435/20; 435/21
[58] Field of Search ............... 435/20, 21; 436/513, 436/825, 826, 530

[56] References Cited

U.S. PATENT DOCUMENTS 3,720,760  2/1984  Bennich et al.
4,031,199  6/1977  Nieschulz et al.
4,845,027  7/1989  Calenoff et al. ................ 436/513

FOREIGN PATENT DOCUMENTS 0083497   7/1983   European Pat. Off.
0131546   1/1985   European Pat. Off.
0135022   3/1985   European Pat. Off.
0367306   5/1990   European Pat. Off.
33338759  10/1984  Fed. Rep. of Germany

OTHER PUBLICATIONS

Lundblad et al., *Chemical Reagents for Protein Modification*, vol. II, Ch. 5, 123-139.
Esen et al., *Anal. Biochem.*, 132:462 (1983).
Jahn et al., *Proc. Natl. Acad. Sci. U.S.A.*, 81:(1984).
Ishikawa et al., *J. Immunoassay* 1:385 (1980).
Conradie et al., *J. Immunol. Method* 59:289 (1983).
Inouye et al., *J. Clin. Microbiol.* 19:259 (1984).
Conroy et al., *Anal. Biochem.* 137:182 (1964).

*Primary Examiner*—Christine Nucker
*Assistant Examiner*—Jeffrey Stucker
*Attorney, Agent, or Firm*—Daniel R. Curry; Wean Khing Wong

[57] ABSTRACT

A method for producing a binding assay device composed of antigens on a cellulose nitrate, cellulose nitrate/acetate or similar solid phase is described. The method involves applying to a solid phase a small amount of an allergen composition, or a pretreated allergen composition, containing a certain concentration of allergen and drying the solution. The device is used by contacting a patient test sample to the immobilized allergen and determining whether or not the test sample contains IgE antibodies for the allergen.

51 Claims, No Drawings

BINDING OF ALLERGENS TO A SOLID PHASE

BACKGROUND OF THE INVENTION

1. Field of the Invention

The present invention relates to the binding of antigens to a solid phase material for use in a diagnostic assay. In particular, the invention increases the effective amount of antigen that can be bound to the solid phase, for example, to a thin microporous sheet of nitrocellulose, thereby making more antigenic sites available for antibody binding in an immunoassay.

2. Background of the Invention

U.S. Pat. No. 3,720,760 discloses that certain immunogenic substances, called allergens, can give rise to allergic reactions in the form of asthma, hay fever, and the like, and that the blood of a patient in whom a given allergen causes an allergic reaction usually contains low concentrations of immunoglobulins, called reagin-immunoglobulins (now usually called "IgE", which term is subsequently used herein), which are directed specifically against that allergen. The patent discloses a test for sensitivity to allergens which involves injecting given allergens into the skin of a patient; a skilled observer then assesses the degree of sensitivity to each of the allergens on the basis of the observed reaction (reddening or swelling of the skin) caused by each allergen. The patent also discloses an "in vivo" test, where the patient inhales an allergen in the form of an aerosol, and the patient is deemed to be sensitive to any allergen that causes hay fever, asthma or like symptoms.

The patent further discloses an in vitro method for determining the presence of IgE in a body fluid. The method involves binding an allergen to fine particles of a copolymer, e.g., a dextran-epichlorohydrin copolymer, by treating the particles with cyanogen bromide, and suspending the particles and an allergen in an aqueous medium. A body fluid to be tested for the presence of IgE directed against that allergen is then contacted with the allergen bound to the copolymer. The product of step (2) is then brought into contact with radiolabeled antibodies which will bind to IgE, if any, that has become bound to the allergen that is bound to the copolymer. The radiation emitted from the solids of step (3), the liquid of step (3), or both can then be measured.

The covalent coupling of antigens, including allergens, to a solid phase was used to prevent or inhibit their removal from the solid phase during the assay procedure. U.S. Pat. No. 4,597,999 describes the covalent coupling of two molecular species to one another, using cross-linking agents having at least two functional groups which are subject to independent activation. Examples of such cross-linking agents include 4-methylazidobenzidimate and N-hydroxysuccinimidyl-azidobenzoate. These cross-linking agents couple spontaneously in the dark to available amino groups, as in aminopropyl glass, aminophenyl glass and aminohexylagarose, and when activated by irradiation with light of a suitable wavelength, these agents also couple with a ligand such as a drug, digoxin, a steroid, or a protein.

U.S. Pat. No. 4,425,434 describes the use of biologically active substances to fill the pores of porous titania spheroids, porous calcium phosphate spheroids, porous zirconia spheroids or similar porous support material, and that the biologically active substance can then be immobilized in the pores by precipitation and cross-linking. The biologically active substance can be a proteinaceous substance, such as an enzyme.

It has been found, however, that the covalent coupling procedures are costly to perform and time consuming. In addition, some coupling procedures can decrease the sensitivity of the assay.

BRIEF DESCRIPTION OF THE PRESENT INVENTION

The present invention involves novel allergen compositions, using a solvent such as deionized or distilled water, containing (in milligrams of protein per milliliter, as determined by a suitable protein test): from about 0.05 to about 4.0 of *Alternaria alternata* allergen; from about 0.5 to about 50 *Aspergillus fumigatus* allergen; from about 0.8 to about 81.6 of Bermuda grass (*Cynodon dactylon*) allergen; from about 0.1 to about 6.0 of birch (*Betula nigra*) allergen; from about 0.6 to about 20.6 of cat (*Felis domesticus*) allergen; from about 0.04 to about 4.5 of mountain cedar (*Juniperus ashei*) allergen; from about 0.1 to about 20.5 of Japanese cedar (*Cryptomeria japonica*) allergen; from about 0.05 to about 10.0 of Cladosporium allergen; from about 1.3 to about 38.4 of dog (*Canis familiarus*) allergen; from about 0.7 to about 22.4 of *Dermatophagoides farinae* (*D. farinae*) allergen; from about 0.6 to about 84.2 of *D. pteronyssinus* allergen; from about 0.1 to about 10.0 of elm (Ulmus) allergen; from about 0.02 to about 0.2 of feather allergen; from about 0.2 to about 20.5 of giant ragweed (*Ambrosia trifida*) allergen; from about 0.4 to about 100 of house dust allergen; from about 0.05 to about 10.5 of June/Kentucky bluegrass (*Poa pratensis*) allergen; from about 0.2 to about 20.5 of lamb's quarters (*Chenopodium album*) allergen; from about 0.1 to about 11.5 of maple (Acer) allergen; from about 0.3 to about 90.4 of mugwort (*Artemesia heterophylla*) allergen; from about 0.1 to about 12 of mulberry (Morus) allergen; from about 0.2 to about 25.5 of oak (Quercus) allergen; from about 0.1 to about 66.8 of olive (*Olea europea*) allergen; from about 1.0 to about 40.0 of Parietaria (*Parietaria officinalis*) allergen; from about 1.7 to about 130.4 of plantain (*Plantago lanceolata*) allergen; from about 0.1 to about 4.8 of Penicillium (*Penicillium notatum*) allergen; from about 0.05 to about 8.5 of perennial rye (*Lolium perenne*) allergen; from about 0.2 to about 20.5 of short ragweed (*Ambrosia elatior*) allergen and from about 0.05 to about 6.6 of timothy (*Phleum pratense*) allergen. Such allergen concentrations have been found optimal for the preparation of immunoassay devices for the detection of anti-IgE antibodies specific for the allergens.

The present invention also involves devices for detecting the presence or amount of IgE in a test sample. The assay devices include a solid phase and an allergen immobilized upon the solid phase, wherein the allergen is typically applied as one of the above allergen compositions. In certain assay devices, the allergen composition is combined with a pretreatment substance such a denaturant, organic solvent, crosslinking agent or concentrated salt solution. It has been unexpectedly found that such allergen pretreatment can enhance allergen immobilization upon the solid phase as well as increase the effective amount of allergen that can be immobilized upon the solid phase. The reaction or binding area of the solid phase can be optionally modified by the addition of a protein blocking reagent. Suitable blocking reagents include equine serum albumin, bovine serum albumin, fish gelatin and casein.

In addition, the present invention describes allergen compositions containing a solvent, an allergen solubilized in the solvent, thereby forming an allergen solution, and a pretreatment substance chosen from denaturants, organic solvents, crosslinking agents or concentrated salt solutions, wherein the allergen solution is combined with the pretreatment substance, and wherein the resultant composition is used for the in vitro detection of the presence or amount of IgE in a test sample. In vitro detection methods can involve: providing a solid phase prepared by applying the novel allergen compositions or pretreated allergen compositions to the solid phase; contacting the sample to be tested to that solid phase, thereby immobilizing allergen-specific IgE antibody from the sample upon the solid phase by forming allergen/antibody complexes; and detecting that immobilized allergen-specific antibody to determine the presence or amount of the antibody in the test sample. Generally, the solid phase is contacted with an indicator reagent to determine the presence or amount of IgE in the test sample, wherein the indicator reagent includes a label conjugated to a binding member that is specific for either the allergen, IgE or an ancillary specific binding member. The label that is selected is not critical to the present invention and is typically chosen from chromogens, catalysts, fluorescent compounds, chemiluminescent compounds, radioactive isotopes, colloidal metallic particles, colloidal selenium particles, dye particles, enzymes, substrates, organic polymer latex particles and liposomes or other vesicles containing signal producing components. The present invention also includes assay kits containing the allergen or allergens of interest immobilized upon the solid phase and a suitable indicator reagent. Optionally, the kit can include assay buffers and wash reagents.

DESCRIPTION OF THE PREFERRED EMBODIMENTS

The present invention is based upon the discovery that an allergen solution can be used to bind an allergen to a solid phase material without the need for covalent linkages. A solid phase so prepared can then be used in an in vitro diagnostic assay for IgE. Suitable solid phase materials include cellulose nitrate or a mixed ester cellulose. In addition, it has been discovered that certain allergen concentrations are optimum insofar as the sensitivity of the assay is concerned.

The invention is also based upon the discovery that many allergens can be pretreated to improve their adherence to the solid phase material. The allergen pretreatment methods of the present invention serve to enhance the binding of the allergen to the solid phase throughout the assay. The allergen pretreatment compositions and methods were also unexpectedly found to increase the amount of allergen which can be bound to the solid phase thereby enabling the binding of allergen in an amount that is optimal for the assay.

The present invention involves novel allergen compositions for the preparation of solid phase devices used in binding assays. The allergen compositions have been unexpectedly found to enhance the binding of the allergen to the solid phase material. As a result, greater amounts of antigen may be immobilized upon the solid phase, thereby providing more antigenic sites for binding antibody during the assay.

The present invention also involves the pretreatment of certain allergen compositions with substances such as denaturants, organic solvents, crosslinking agents and concentrated salt solutions. Pretreatment of an allergen composition with one or more of these substances was unexpectedly found to enhance the adherence of the allergen to a solid phase throughout the assay procedure which may include multiple washing steps or other manipulations which could otherwise dislodge the allergen from the solid phase. In addition, the pretreatment of the allergen improves their binding performance at elevated temperatures often used in binding assays.

Suitable denaturants include, but are not limited to: acids such as hydrochloric acid (HCl) and acetic acid. Organic solvents, such as tetrahydrofuran, are suitable for allergen pretreatment. Concentrated salt solutions, such as concentrated solutions of sodium chloride (NaCl), are also suitable for allergen pretreatment according to the present invention. Suitable cross-linking agents for the pretreatment of allergens include, but are not limited to: formaldehyde, glutaraldehyde and 1-ethyl-3-(3-dimethylaminopropyl)carbodiimide (EDAC).

Allergen compositions combined with such pretreatment substances are then used in the production of novel solid phase assay devices. The allergen compositions or pretreated allergen compositions are applied to a solid phase material upon which the allergen composition is dried and thereby immobilized. The solid phase devices can then be used in binding assays which include, but are not limited to, competitive assays, sandwich assays and indirect assays, and include both forward and reverse assay formats.

In a preferred embodiment of the present invention, the allergen of interest is immobilized upon a solid phase material made of nitrocellulose or a nitrocellulose derivative or compound, such as cellulose acetate/nitrate mixed ester cellulose. The maximum binding capacity of nitrocellulose for the protein bovine serum albumin is about 140 $\mu g/cm^2$. This binding capacity value is converted according to the desired size of the solid phase reaction or binding area of the present invention, and a value of 2.2 mg/ml is obtained. This concentration is used as the starting protein concentration for all allergens, but the optimum allergen concentration may be above or below this value. Different concentrations of allergen solutions are pretreated, immobilized on nitrocellulose and tested with a positive test sample, as described in the specific examples which follow. The allergen concentration is adjusted such that when concentration is plotted against signal a parabolic curve is obtained, and the optimum allergen concentration can be determined from the maximum detected signal.

The allergen protein concentrations which were tested ranged from about 0.05 milligrams of allergen per milliliter of solvent, prior to pretreatment, to about 170 mg/mL. The most effective concentration ranges for each of the allergens tested are presented in the specific examples which follow.

The invention will be more fully understood from the following examples, which constitute the best modes presently contemplated by the inventors. It is to be understood, however, that the examples are presented solely for the purpose of illustration, and are not to be construed as limiting.

Before proceeding with the description of the specific embodiments of the present invention, a number of terms will be defined. All allergen contents herein refer to the protein content of the allergen solutions, determined using a suitable protein test such as Coomasie blue or Ninhydrin as are well-known in the art.

The term "analyte" refers to the substance to be detected in or separated from test sample. The analyte can be any substance for which there exists a naturally occurring specific binding member or for which a specific binding member can be prepared. In addition, the analyte may bind to more than one specific binding member. "Analyte" also includes any antigenic substances, haptens, antibodies, and combinations thereof. In the present invention, the main analytes to be detected or measured are IgE antibodies.

The term "test sample" refers to virtually any liquid sample. The test sample can be derived from any desired source, such as a physiological fluid, for example, blood, saliva, ocular lens fluid, cerebral spinal fluid, sweat, urine, milk, ascites fluid, mucous, synovial fluid, peritoneal fluid, amniotic fluid or the like. The liquid test sample can be pretreated prior to use, such as preparing plasma from blood, diluting viscous liquids, or the like; methods of treatment can also involve separation, filtration, distillation, concentration, inactivation of interfering components, and the addition of reagents. In addition, a solid can be used once it is modified to form a liquid medium.

The term "specific binding member" refers to a member of a specific binding pair, i.e., two different molecules wherein one of the molecules through chemical or physical means specifically binds to the second molecule. In addition to antigen and antibody specific binding pairs such as the allergen and antibody pair, other specific binding pairs include, biotin and avidin, carbohydrates and lectins, complementary nucleotide sequences, complementary peptide sequences, effector and receptor molecules, enzyme cofactors and enzymes, enzyme inhibitors and enzymes, a peptide sequence and an antibody specific for the sequence protein, polymeric acids and bases, dyes and protein binders, peptides and specific protein binders (e.g., ribonuclease, S-peptide and ribonuclease S-protein), and the like. Furthermore, specific binding pairs can include members that are analogs of the original specific binding member, for example an analyte-analog. If the specific binding member is an immunoreactant it can be, for example, an antibody, antigen, hapten, or complex thereof. If an antibody is used, it can be a monoclonal or polyclonal antibody, a recombinant protein or antibody, a mixture or mixtures or a fragment or fragments thereof, as well as a mixture of an antibody and other specific binding members. The details of the preparation of such antibodies and their suitability for use as specific binding members are well-known to those skilled-in-the-art.

An "indicator reagent", as used herein, refers to a label attached to a specific binding member. The indicator reagent produces a detectable signal at a level relative to the amount of an analyte in the test sample. Generally, the indicator reagent is detected or measured after it is captured on the solid phase material, but the unbound indicator reagent can also be measured to determine the result of an assay. The specific binding member component of the indicator reagent enables the indirect binding of the label to the analyte, to an ancillary specific binding member, to the capture reagent or to a complex thereof.

The term "label" refers to any substance which is attached to a specific binding member and which is capable of producing a signal that is detectable by visual or instrumental means. Suitable labels for use in the present invention can include chromogens; catalysts; fluorescent compounds; chemiluminescent compounds; radioactive isotopes; direct visual labels including colloidal metallic and non-metallic particles, dye particles, enzymes or substrates, or organic polymer latex particles; liposomes or other vesicles containing signal producing substances; and the like.

Many enzymes suitable for use as labels are disclosed in U.S. Pat. No. 4,275,149, columns 19–23, herein incorporated by reference. For example, an enzyme/substrate signal producing system useful in the present invention is the enzyme alkaline phosphatase wherein the substrate used can be 5-bromo-4-chloro-3-indolyl phosphate or a derivative or analog thereof. If horseradish peroxidase is used, o-Phenylenediamine or 4-chloronaphthol is added as an enzyme substrate to form a colored product which can be detected and/or measured visually or instrumentally.

In an alternative signal producing system, the label can be a fluorescent compound where no enzymatic manipulation of the label is required to produce a detectable signal. Fluorescent molecules such as fluorescein, phycobiliprotein, rhodamine and their derivatives and analogs are suitable for use as labels in this system.

An especially preferred class of labels includes the visually detectable, colored particles which enable a direct colored readout of the presence or concentration of the analyte in the test sample without the need for using additional signal producing reagents. Materials for use as such particles include colloidal metals, such as gold, and dye particles as disclosed in U.S. Pat. Nos. 4,313,734 and 4,373,932. The preparation and use of non-metallic colloids, such as colloidal selenium particles, are disclosed in co-owned and copending U.S. patent application Ser. No. 072,084, filed July 9, 1987, which is incorporated by reference herein in its entirety. Organic polymer latex particles for use as labels are disclosed in co-owned and copending U.S. patent application Ser. No. 248,858, filed Sept. 23, 1988, which is incorporated by reference herein in its entirety.

A variety of different indicator reagents can be formed by varying either the label or the specific binding member; it will be appreciated by one skilled-in-the-art that the choice involves consideration of the analyte to be detected and the desired means of detection. The selection of a particular label is not critical, so long as the label is capable of generating a detectable signal either by itself or in conjunction with one or more additional signal producing components. The details of the preparation of such label/specific binding member conjugates are well-known to those skilled-in-the-art.

The term "signal producing component" refers to any substance capable of reacting with another assay reagent or the analyte to produce a reaction product or signal that indicates the presence of the analyte and that is detectable by visual or instrumental means. "Signal production system", as used herein, refers to the group of assay reagents that are needed to produce the desired reaction product or signal. For example, one or more signal producing components can be used to react with a label and generate the detectable signal, i.e., when the label is an enzyme, amplification of the detectable signal is obtained by reacting the enzyme with one or more substrates or additional enzymes to produce a detectable reaction product.

The term "capture reagent" refers to a capture binding member which is attached to a solid phase material to enable the separation of the analyte or indicator reagent, that is bound thereto, from unbound analyte and assay reagents. Typically, the attachment of the capture binding member to the solid phase material is substantially irreversible.

In forming a capture reagent to be used in an assay, once the capture binding member, e.g., allergen, is immobilized upon the solid phase, the remaining surface area of the solid phase is generally blocked with a suitable inactivating solution, such as bovine or equine serum albumin, casein or other proteinaceous material, to prevent non-specific binding of protein to the solid phase when the reaction mixture containing a specific binding member is contacted to the solid phase. The solid phase is then washed with an appropriate solution to remove any excess blocking solution and/or unbound capture binding member.

Once complex formation occurs between the assay components, the solid phase can be used as a separation mechanism. For example, the reaction mixture can be contacted to the capture reagent, and the solid phase material retains the newly formed reaction complex(es).

Assay devices can have many configurations, several of which are dependent upon the material chosen for the solid phase. The term "solid phase material" refers to any suitable chromatographic, bibulous, porous or capillary material or other conventional solid material, well-known to those skilled-in-the-art for use in immobilizing specific binding members. Solid phase materials can include fiberglass, nylon or cellulose or derivatives thereof, such as cellulose nitrate or a cellulose acetate/cellulose nitrate mixed ester cellulose. The solid phase, however, is not limited to porous materials. The solid phase material can also include, without limitation, polymeric or glass beads, microparticles, tubes, sheets, plates, slides, magnetic beads, a microtitre plate with one or more reaction wells or a glass or plastic test tube, or the like.

Natural, synthetic or naturally occurring materials that are synthetically modified, can be used as a solid phase material including polysaccharides, e.g., cellulose materials including paper, cellulose and cellulose derivatives such as cellulose acetate, nitrocellulose and cellulose acetate/nitrate mixed ester cellulose; silica; fiberglass; inorganic materials such as deactivated alumina, diatomaceous earth or other inorganic finely divided material uniformly dispersed in a porous polymer matrix, with polymers such as vinyl chloride, vinyl chloride-propylene copolymer, and vinyl chloride-vinyl acetate copolymer; cloth, both naturally occurring (e.g., cotton) and synthetic (e.g., nylon); porous gels such as silica gel, agarose, dextran and gelatin; polymeric films such as polyacrylamide; magnetic particles; microtitre plates; polystyrene tubes; protein binding membranes; agarose; Sephadex ® (Pharmacia Fine Chemicals, Inc., Piscataway, N.J.); Trisacryl (Pointet-Girard, France); silicon particles; porous fibrous matrixes; and the like. The solid phase material should have a reasonable inherent strength or strength can be provided by means of a support, and it should not interfere with the production of a detectable signal.

Optionally, the specific binding member of the capture reagent can be affixed to particles, e.g., microparticles. These microparticles can serve as the solid phase material and be retained in a column, suspended in a mixture of soluble reagents and test sample, or retained and immobilized by another solid phase base material. By "retained and immobilized" is meant that the microparticles, associated with the solid phase base material, are not capable of substantial movement to positions elsewhere within that material. The microparticles can be selected by one skilled-in-the-art from any suitable type of particulate material including those composed of polystyrene, polymethylacrylate, polypropylene, polytetrafluoroethylene, polyacrylonitrile, polycarbonate or similar materials. The size of the microparticles is not critical, although it is preferred that the average diameter be smaller than the average pore size of the solid phase base material if such is used.

The term "ancillary specific binding member" refers to a specific binding member used in addition to the specific binding members of the capture reagent and the indicator reagent. One or more ancillary specific binding members can be used in an assay. For example, an ancillary specific binding member can be used in an assay where the specific binding member of the indicator reagent is capable of binding the ancillary specific binding member which is in turn capable of binding the analyte.

The present invention is concerned with immunoassays. Therefore, the following discussion of immunoassays and definitions of terms often used with respect to immunoassays are set forth to facilitate the understanding of the disclosure and claims hereof.

In accordance with one method of the present invention, a sandwich assay can be performed wherein a capture reagent can include an allergen which has been bound to a solid phase material. The capture reagent is contacted with a test sample, suspected of containing the analyte, and an indicator reagent containing an analyte-specific binding member conjugated to a label. The reagents can be contacted to the sample simultaneously or added sequentially. A binding reaction results in the formation of a capture reagent/analyte/indicator reagent complex. The assay may also involve a washing step to separate the resultant complex from the excess reagents and test sample. Either the unreacted indicator reagent or the complex retained upon the solid phase is then observed to detect or measure the amount of label associated therewith. If analyte is present in the sample, then label will be present on the solid phase material. The amount of label on the solid phase is proportional to the amount of analyte in the sample.

The present invention also can be used to conduct a competitive assay. In one example of a competitive configuration, the capture reagent again includes a specific binding member (allergen) which has been attached to a solid phase material. The capture reagent is contacted with both test sample and an indicator reagent that includes an analyte or analyte analog which has been labeled with a signal generating compound. The indicator reagent and analyte then compete in binding to the capture reagent. The competitive binding reaction results in the formation of capture reagent/analyte complexes or capture reagent/indicator reagent complexes. The capture reagent/indicator reagent complexes can be detected via the label of the indicator reagent. In the competitive assay, the amount of label that becomes associated with the solid phase is inversely proportional to the amount of analyte in the sample.

The present invention can also be used in indirect immunoassays involving one or more ancillary specific binding members. For example, an indirect sandwich immunoassay with the formation of a capture reagent/analyte/anti-analyte antibody/indicator reagent complex can be performed, wherein the indicator reagent is a specific binding partner for the ancillary specific binding member which is specific for the analyte. The present invention can also be used in forward and reverse immunoassay protocols

EXAMPLES

Example 1

In this experiment, *Alternaria alternata* allergen was pretreated for binding to a solid phase material. A 37% aqueous formaldehyde solution (12.5 µL) was mixed with 100 microliters of a solution of *Alternaria alternata* (28.8 µg/mL) in deionized water. The amount of formaldehyde effective for pretreatment was found to range from about 10 µL to about 20 µL when the 37% aqueous formaldehyde solution was used. The resulting mixture was incubated at 4° C. for about 10 hours, and the incubated composition was allowed to stand for 30 to 60 minutes at about 20° C. The mixture was then centrifuged, and the resultant supernatant, a pretreated *Alternaria alternata* allergen composition, was decanted. The pretreated composition was poured onto a disc of microporous cellulose nitrate (about 140 µm thick and about 3 mm in diameter) and allowed to dry. The allergen was thereby immobilized upon the solid phase material. The remaining surface of the disc was then blocked with a ten percent horse serum solution.

The solid phase bound allergen, or *Alternaria alternata* capture reagent, was then used in an enzyme immunoassay ("EIA"). The EIA method included the following steps. The sample to be tested (e.g., serum) was contacted to the capture reagent, thereby immobilizing allergen-specific IgE antibodies upon the solid phase. Optionally, the antibody immobilization step was followed by a wash step to remove unbound sample. The capture reagent was then contacted to an enzyme-labeled anti-IgE antibody (indicator reagent) which bound to that IgE from the sample, if any, which had bound to the solid phase. The solid phase was then washed to remove unbound indicator reagent. The solid phase was contacted to an enzyme substrate signal producing component such that the enzyme component of the complexed indicator reagent would react with the substrate to produce a detectable signal. Prior to detection, the solid phase may undergo a third washing to remove unbound substrate. The signal which was detected was directly related to the amount of allergen-specific IgE in the test sample.

In one EIA procedure, the enzyme label was alkaline phosphatase, the substrate was 5-bromo-4-chloro-3-indolylphosphate and the detection or measurement step was performed with a reflectance spectrophotometer. The disc turned dark blue upon the addition of substrate to the solid phase, i.e., a positive assay result, when the serum sample contained IgE antibody specific to *Alternaria alternata*. The assay procedure was repeated using serum from different patients, and the results were found to correlate with the results obtained for the same serum samples using alternate tests, such as a radio-allergo-sorbent test (RAST) or a skin prick test as are well-known in the art.

Example 2

In this experiment, the nitrocellulose disc used as the solid phase was one of many discs on a laminate composed of a mylar sheet to which a sheet of nitrocellulose had been glued. A circular shape was embossed onto the nitrocellulose sheet to form each of the discs. The micropores in the nitrocellulose sheet had diameters of about 450 nanometers. Each individual disc had a separate allergen attached thereto. Thus, the device could be used to detect the presence of antibodies to multiple allergens.

Example 3

The procedure of Example 1 was repeated using 100 microliter portions of solutions containing birch allergen (137 µg) or dog allergen (280 µg) which were mixed with a 37% aqueous formaldehyde solution (12.5 µL) and incubated thereby forming pretreated allergen compositions. The amount of formaldehyde effective for pretreatment was found to range from about 10 µL to about 15 µL when the 37% aqueous formaldehyde solution was used. The compositions were used substantially in accordance with the procedures described in Examples 1 and 2 to produce devices which were then used to test serum samples. The assay results were found to correlate with the results of testing the same serum samples by other means: the disc turned dark blue when the serum sample contained IgE specific for the allergen immobilized upon the solid phase.

Example 4

Tetrahydrofuran (25 µL) was mixed with 100 microliters of a solution containing Bermuda grass allergen (510 µg) in deionized water. The amount of tetrahydrofuran effective for pretreatment was found to range from about 10 µL to about 50 µL. The resulting mixture was incubated at 4° C. for about 10 hours, and the incubated composition was allowed to stand at about 20° C. for 30 to 60 minutes. The solution was then centrifuged, and the resultant supernatant, a pretreated Bermuda grass allergen composition, was decanted.

The procedure was repeated using 100 microliter-portions of solutions which contained Japanese cedar allergen (150 µg), June/Kentucky blue grass allergen (545 µg), perennial rye allergen (433 µg) or timothy allergen (43 µg) in deionized water. The pretreated allergen compositions were used to produce solid phase discs and were used in immunoassays substantially in accordance with the procedure described in Example 1. The assay results were found to correlate with the results of testing the same serum samples by other means: the disc turned dark blue when the serum sample contained IgE specific for the allergen immobilized upon the solid phase.

Example 5

A 37 percent aqueous formaldehyde solution (15.6 µg) was mixed with 100 microliters of a solution containing mountain cedar allergen (733 µg) in deionized water. The resulting mixture was incubated at about 20° C. for approximately 30 minutes. Tetrahydrofuran (28.7 µL) was then mixed with the incubated solution. The amount of formaldehyde effective for pretreatment was found to range from about 10 µL to about 20 µL, and the amount of tetrahydrofuran was found to range from about 10 µL to about 50 µL. The mixture was incubated for about 10 hours at 4° C. and was allowed to stand at about 20° C. for 30 to 60 minutes. The mixture was then centrifuged, and the resultant supernatant, a pretreated cedar allergen composition, was decanted.

This allergen pretreatment procedure was repeated, using 100 microliter-portions of solutions containing oak allergen (729 µg) or olive allergen (1670 µg), in deionized water, in place of the mountain cedar allergen. The pretreated allergen compositions were then used to produce immunoassay devices substantially in accordance with the procedures described in Examples 1 and 2. The EIA results were found to correlate with the results of testing of the same serum samples by other means: the disc turned dark blue when the serum sample contained IgE specific for the allergen immobilized upon the solid phase.

Example 6

Aqueous NaCl (5M, 12 μL) was mixed with 100 microliters of a solution containing Cladosporium (960 μg) in deionized water. The resulting mixture was incubated at about 4° C. for about 10 hours, and the incubated composition was then allowed to stand at about 20° C. for 30 to 60 minutes. The mixture was then centrifuged, and the resultant supernatant, a pretreated Cladosporium allergen composition, was decanted. Depending upon the molar value of the concentrated salt solution used, which value ranged from about 0.5M to about 10M, the amount of aqueous NaCl effective for pretreatment ranged from about 10 μL to about 20 μL.

The procedure was repeated using 100 microliters of a solution containing feather allergen (7 μg) in deionized water. The pretreated allergen compositions were then used to produce assay devices and were used in immunoassays substantially in accordance with the protocol described in Example 1. The assay results using the compositions and devices of the present invention were found to correlate with the results of testing the same serum samples by other means: the disc turned dark blue when the serum contacted thereto contained IgE specific for the allergen immobilized upon the solid phase.

Example 7

An aqueous solution of 1-ethyl-3-(3-dimethylaminopropyl)carbodiimide (EDAC, 10 μL at 50 mg/mL) was mixed with 100 microliters of a solution containing D. farinae (280 μg) in deionized water. The amount of EDAC effective for the first stage of pretreatment ranged from about 5.0 μL to about 15 μL. The resulting mixture was incubated at about 22° C. for about 15 minutes. A two microliter portion of a solution containing sodium borohydride (20 mg/mL, $NaBH_4$) in 10 μM phosphate buffered saline (pH 7) was mixed with the incubated solution, and the mixture was further incubated at about 4° C. for 10 hours. The amount of $NaBH_4$ effective for the second stage of pretreatment ranged from about 1.0 μL to about 5.0 μL. The mixture was then allowed to stand at about 20° C. for approximately 30 to 60 minutes. The mixture was centrifuged, and the resultant supernatant, a pretreated D. farinae allergen composition, was decanted.

The procedure was repeated using 100 microliters of a solution containing D. pteronyssinus (263 μg) in deionized water. The pretreated allergen compositions were used substantially in accordance with the procedures described in Example 1 to produce treated discs for immunoassays. The EIA results were found to correlate with the results of testing the same serum samples by other means: the disc turned dark blue when the serum sample contacted thereto contained IgE specific for the allergen immobilized upon the solid phase.

Example 8

One hundred percent acetic acid (12.5 μL, with effective amounts ranging from about 5.0 μL to about 30 μL) was mixed with 100 microliters of a solution containing lamb's quarters allergen (1176 μg) in deionized water. The resultant mixture was incubated at about 22° C. for approximately five minutes, after which time 6N aqueous NaOH was added to adjust the pH to 7. The neutralized solution was incubated at about 4° C. for 10 hours, and was then allowed to stand at about 20° C. for 30 to 60 minutes. The mixture was then centrifuged, and the resultant supernatant, a pretreated lamb's quarters allergen composition, was decanted.

The procedure was repeated using 100 microliters of a solution containing mulberry allergen (40 μg) in deionized water. The pretreated allergen compositions were used to produce treated discs for enzyme immunoassays substantially in accordance with the procedures described in Example 1. The assay results were found to correlate with the results of testing the same serum samples by other means: the disc turned dark blue when the serum sample contacted thereto contained IgE specific for the allergen immobilized upon the solid phase.

Example 9

A solution of 6N aqueous HCl (24 μL, with effective amounts ranging from about 6.0 μL to about 30 μL) was mixed with 100 microliters of a solution containing Penicillium (120 μg). The resulting mixture was incubated for approximately five minutes at about 20° C., after which time 6N aqueous NaOH was added to adjust the pH to 7. The neutralized solution was incubated at 4° C. for 10 hours and was then allowed to stand at about 20° C. for 30 to 60 minutes. The mixture was then centrifuged, and the resultant supernatant, a pretreated Penicillium allergen composition, was decanted.

The allergen pretreatment procedure was repeated with 100 microliters of a solution containing Parietaria allergen (400 μg) in deionized water. The solutions were then used substantially in accordance with the procedures described in Example 1 to produce discs and to test serum samples in an EIA. The assay results were found to correlate with the results of testing the same serum samples by other means: the disc turned dark blue when the serum contacted thereto contained IgE specific for the allergen immobilized upon the solid phase.

Example 10

Untreated allergen compositions included from about 0.5 to about 50 Aspergillus allergen; from about 0.6 to about 20.6 of cat allergen; from about 0.1 to about 10.0 of elm allergen; from about 0.4 to about 100 of house dust allergen; from about 0.1 to about 11.5 of maple allergen; from about 0.3 to about 90.4 of mugwort allergen and from about 1.7 to about 130.4 of plantain allergen in deionized water.

The solutions were then used substantially in accordance with the procedures described in Example 1 to produce discs and to test serum samples in an EIA. The assay results were found to correlate with the results of testing the same serum samples by other means: the disc turned dark blue when the serum sample contained IgE specific for the allergen immobilized upon the solid phase.

Example 11

Pretreated allergen compositions, which were produced as described in Examples 1, and 3 through 9, and which differed from one another with respect to allergen content, were used to test for IgE in a series of serum samples. Upper and lower allergen concentration limits were set by classifying a pretreated allergen composition as either "too dilute" if that composition failed to produce a maximum positive IgE test result with a serum sample which had tested positive with a more concentrated allergen solution, or "too concentrated" if the composition failed to produce a maximum positive IgE test result with a serum sample which had tested positive with a less concentrated allergen solution. The allergen concentrations tested ranged from about 0.05 milligrams of allergen per milliliter of water, prior to pretreatment, to about 170 milligrams/milliliter. The test results are presented in Table 1 and illustrate the most effective concentration ranges for each of the allergens tested.

TABLE 1

| Allergen | Effective concentration range (protein content in solution) |
|---|---|
| Alternaria alternata allergen | from 0.05 to 4.0 mg/mL |
| Aspergillus fumigatus allergen | from 0.5 to 50.0 mg/mL |
| Bermuda grass allergen | from 0.8 to 81.6 mg/mL |
| birch allergen | from 0.1 to 6.0 mg/mL |
| mountain cedar allergen | from 0.04 to 4.5 mg/mL |
| Japanese cedar allergen | from 0.1 to 20.5 mg/mL |
| Cladosporium allergen | from 0.05 to 38.4 mg/mL |
| cat allergen | from 0.6 to 20.6 mg/mL |
| dog allergen | from 1.3 to 38.4 mg/mL |
| D. farinae allergen | from 0.7 to 22.4 mg/mL |
| D. pteronyssinus allergen | from 0.6 to 84.2 mg/mL |
| elm allergen | from 0.1 to 146.0 mg/mL |
| feather allergen | from 0.02 to 0.2 mg/mL |
| giant ragweed allergen | from 0.2 to 148.2 mg/mL |
| house dust allergen | from 0.4 to 100 mg/mL |
| June/Kentucky bluegrass allergen | from 0.05 to 21.8 mg/mL |
| lamb's quarters allergen | from 0.2 to 47.0 mg/mL |
| maple allergen | from 0.1 to 166.3 mg/mL |
| mugwort allergen | from 0.3 to 90.4 mg/mL |
| mulberry allergen | from 0.1 to 12 mg/mL |
| oak allergen | from 0.2 to 29.2 mg/mL |
| olive allergen | from 0.1 to 66.8 mg/mL |
| Parietaria allergen | from 1.0 to 40.0 mg/mL |
| plantain allergen | from 1.7 to 130.4 mg/mL |
| Penicillium allergen | from 0.1 to 4.8 mg/mL |
| perennial rye allergen | from 0.05 to 17.3 mg/mL |
| short ragweed allergen | from 0.2 to 151.6 mg/mL |
| timothy allergen | from 0.05 to 6.6 mg/mL |

In this manner, the optimum concentration of allergen was determined for the production of solid phase assay devices.

It will be appreciated by one skilled-in-the-art that the concepts of the present invention are equally applicable to many different allergens (specific binding members), solid phase materials and immunoassay protocols. It will also be appreciated that the selection of any given label, ancillary binding member or solid phase material is generally not critical to the present invention. The materials are selected to optimize the results provided by the chosen assay configuration. The embodiments described herein are intended as examples rather than as limitations. Thus, the description of the invention is not intended to limit the invention to the particular embodiments described in detail, but it is intended to encompass all equivalents and subject matter within the spirit and scope of the invention as described above and as set forth in the following claims.

What is claimed is:

1. A device, for detecting the presence or amount of IgE in a test sample, comprising:
    a) a solid phase comprising a material selected from the group consisting of: nitrocellulose, nitrocellulose derivatives, nitrocellulose compounds, or combinations thereof, and
    b) at least one allergen immobilized upon said solid phase, wherein said allergen was applied as an allergen composition and
    wherein said allergen composition is formed from the combination of said allergen with a pretreatment substance selected from the group consisting of: denaturants excluding organic solvents and concentrated salt solutions; organic solvents; crosslinking agents; concentrated salt solutions; and combinations thereof.

2. The device according to claim 1, wherein said pretreatment substance is hydrochloric acid or acetic acid.

3. The device according to claim 1, wherein said pretreatment substance is tetrahydrofuran.

4. The device according to claim 1, wherein said pretreatment substance is a concentrated sodium chloride solution.

5. The device according to claim 1, wherein said pretreatment substance is formaldehyde, glutaraldehyde or 1-ethyl-3-(3-dimethylaminopropyl)carbodiimide.

6. The device according to claim 1, where said solid phase is selected from the group consisting of cellulose, cellulose derivatives, silica, fiberglass, a porous polymer matrix, porous gels, polymeric films, agarose and porous fibrous matrixes.

7. The device according to claim 1, where said solid phase is selected from the group consisting of cellulose acetate, nitrocellulose and cellulose acetate/nitrate mixed ester cellulose.

8. The device according to claim 1, further comprising a protein blocking reagent on said solid phase.

9. A method for producing a device according to claim 1, comprising the steps of:
    a) forming the allergen composition by pretreating the allergen with a substance selected from the group consisting of: denaturants excluding organic solvents and concentrated salt solutions; organic solvents; crosslinking agents; concentrated salt solutions; and combinations thereof
    b) applying said allergen composition to said solid phase, and
    c) drying said allergen composition on said solid phase, thereby immobilizing said allergen upon said solid phase.

10. The method according to claim 9, further comprising the step of applying a protein blocking reagent to said solid phase.

11. The method according to claim 10, wherein said protein blocking reagent is selected from the group consisting of equine serum albumin, bovine serum albumin, fish gelatin and casein.

12. The method according to claim 11, wherein said pretreatment substance is hydrochloric acid or acetic acid.

13. The method according to claim 11, wherein said pretreatment substance is tetrahydrofuran.

14. The method according to claim 11, wherein said pretreatment substance is a concentrated sodium chloride solution.

15. The method according to claim 11, wherein said pretreatment substance is formaldehyde, glutaraldehyde or 1-ethyl-3-(3-dimethylaminopropyl)carbodiimide.

16. The method according to claim 9, where said solid phase is selected from the group consisting of cellulose, cellulose derivatives, silica, fiberglass, a porous polymer matrix, porous gels, polymeric films, agarose and porous fibrous matrixes.

17. The method according to claim 9, where said solid phase is selected from the group consisting of cellulose acetate, nitrocellulose and cellulose acetate/-nitrate mixed ester cellulose.

18. The device of claim 1, wherein the allergen composition contains, on the basis of allergen protein in water,
  i) from 0.05 to 4.0 mg/mL of Altenaria allergen,
  ii) from 0.05 to 50 mg/mL of Aspergillus allergen,
  iii) from 0.8 to 81.6 mg/mL of Bermuda grass allergen,
  iv) from 0.1 to 6.0 mg/mL of birch allergen,
  v) from 0.6 to 20.6 mg/mL of cat allergen,
  vi) from 0.04 to 4.5 mg/mL of mountain cedar allergen,
  vii) from 0.1 to 20.5 mg/mL of Japanese cedar allergen,
  viii) from 0.05 to 38.4 mg/mL of Cladosporium allergen,
  ix) from 1.3 to 38.4 mg/mL of dog allergen,
  x) from 0.7 to 22.4 mg/mL of D. farinase allergen,
  xi) from 0.6 to 84.2 mg/mL of D. pteronyssinus allergen,
  xii) from 0.1 to 146.0 mg/mL of elm allergen,
  xiii) from 0.02 to 0.2 mg/mL of feather allergen,
  xiv) from 0.2 to 148.2 mg/mL of giant ragweed allergen,
  xv) from 0.4 to 100 mg/mL of house dust allergen,
  xvi) from 0.05 to 21.8 mg/mL of June/Kentucky bluegrass allergen,
  xvii) from 0.2 to 47.0 mg/mL of lamb's quarters allergen,
  xviii) from 0.1 to 166.3 mg/mL of maple allergen,
  xix) from 0.3 to 90.4 mg/mL of mugwort allergen,
  xx) from 0.1 to 12 mg/mL of mulberry allergen,
  xxi) from 0.2 to 29.2 mg/mL of oak allergen,
  xxii) from 0.1 to 66.8 mg/mL of olive allergen,
  xxiii) from 1.0 to 40.0 mg/mL of Parietaria allergen,
  xxiv) from 1.7 to 130.4 mg/mL of plantain allergen,
  xxv) from 0.1 to 4.8 mg/mL of Penicillium allergen,
  xxvi) from 0.05 to 17.3 mg/mL of perennial rye allergen,
  xxvii) from 0.2 to 151.6 mg/mL of short ragweed allergen, or
  xxviii) from 0.05 to 6.6 mg/mL of timothy allergen,.

19. An allergen composition, comprising:
  a) a solvent; and
  b) an allergen solubilized in said solvent, thereby forming an allergen solution; and
  c) wherein said allergen solution is combined with a pretreatment substance to form an allergen composition; wherein said pretreatment substance is selected from the group consisting of: denaturants excluding organic solvents and concentrated salt solutions; organic solvents; crosslinking agents; concentrated salt solutions; and combinations thereof;
the allergen composition is used for the in vitro detection of the presence or amount of IgE in a test sample.

20. The allergen composition according to claim 19, wherein:
  a) said allergen is selected from the group consisting of Altenaria allergen, birch allergen and dog allergen; and
  b) said pretreatment substance is a formaldehyde solution.

21. The allergen composition according to claim 20, wherein said pretreatment substance is about 10 to about 20 microliters of a 37 percent formaldehyde solution.

22. The allergen composition according to claim 20, wherein said pretreatment substance is about 12.5 microliters of a 37 percent formaldehyde solution.

23. The allergen composition according to claim 19, wherein:
  a) said allergen is selected from the group consisting of Bermuda grass allergen; Japanese cedar allergen; June/Kentucky bluegrass allergen; perennial rye allergen; and timothy allergen; and
  b) said pretreatment substance is tetrahydrofuran.

24. The allergen composition according to claim 23, wherein said pretreatment substance is about 10 to about 50 microliters of tetrahydrofuran.

25. The allergen composition according to claim 23, wherein said pretreatment substance is about 25 microliters of tetrahydrofuran.

26. The allergen composition according to claim 19, wherein:
  a) said allergen is selected from the group consisting of mountain cedar allergen; oak allergen and olive allergen; and
  b) said pretreatment substance comprises tetrahydrofuran and a formaldehyde solution.

27. The allergen composition according to claim 26, wherein said pretreatment substance comprises about 10 to about 50 microliters of tetrahydrofuran and about 10 to about 20 microliters of a 37 percent formaldehyde solution.

28. The allergen composition according to claim 26, wherein said pretreatment substance comprises about 25 microliters of tetrahydrofuran and about 15 microliters of a 37 percent formaldehyde solution.

29. The allergen composition according to claim 19, wherein:
  a) said allergen is selected from the group consisting of Cladosporium allergen and feather allergen; and
  b) said pretreatment substance is about 0.5M to about 10M sodium chloride solution.

30. The allergen composition according to claim 29, wherein said pretreatment substance is about 10 to about 20 microliters of 5M sodium chloride.

31. The allergen composition according to claim 29, wherein said pretreatment substance is about 12 microliters of 5M sodium chloride.

32. The allergen composition according to claim 19, wherein:
  a) said allergen is selected from the group consisting of *Dermatophagoides farinae* allergen and *D. pteronyssinus* allergen; and
  b) said pretreatment substance comprises 1-ethyl-3-(3-dimethylaminopropyl)carbodiimide and sodium borohydride.

33. The allergen composition according to claim 32, wherein said pretreatment substance comprises about 5.0 to about 15 microliters of 50 mg/mL 1-ethyl-3-(3-dimethylaminopropyl)carbodiimide and about 1.0 to about 5.0 microliters of 20 mg/mL sodium borohydride.

34. The allergen composition according to claim 32, wherein said pretreatment substance comprises about 10 microliters of 50 mg/mL 1-ethyl-3-(3-dimethylaminopropyl)carbodiimide and about 2.0 microliters of 20 mg/mL sodium borohydride.

35. The allergen composition according to claim 19, wherein:

a) said allergen is selected from the group consisting of lamb's quarters allergen and mulberry allergen; and b) said pretreatment substance comprises acetic acid, buffered to about a pH of 7.

36. The allergen composition according to claim 35, wherein said pretreatment substance comprises about 5.0 to about 30 microliters of acetic acid and 6N aqueous sodium hydroxide at about a pH of 7.

37. The allergen composition according to claim 35, wherein said pretreatment substance comprises about 12.5 microliters of acetic acid and 6N aqueous sodium hydroxide to a pH of 7.

38. The allergen composition according to claim 19, wherein:

a) said allergen is selected from the group consisting of Parietaria allergen and Penicillium allergen; and b) said pretreatment substance comprises hydrochloric acid, buffered to about a pH of 7.

39. The allergen composition according to claim 38, wherein said pretreatment substance comprises about 6.0 to about 30 microliters of 6N hydrochloric acid and 6N aqueous sodium hydroxide at about a pH of 7.

40. The allergen composition according to claim 38, wherein said pretreatment substance comprises about 24 microliters of 6N hydrochloric acid and 6N aqueous NaOH at about a pH of 7.

41. An allergen composition, comprising:

a) a solvent;

b) an allergen solubilized in said solvent, thereby forming an allergen solution; and c) a pretreatment substance selected from the group consisting of: denaturants excluding organic solvents and concentrated salt solutions; organic solvents; crosslinking agents; concentrated salt solutions; and combinations thereof;

wherein said allergen solution is combined with said pretreatment substance to form an allergen composition, and wherein the allergen composition is used for the in vitro detection of the presence or amount of IgE in a test sample.

42. A method for determining the presence or amount of IgE in a test sample, comprising the steps of:

a) providing at least one allergen immobilized upon a solid phase comprising a material selected from the group consisting of nitrocellulose, nitrocellulose derivatives, nitrocellulose compounds, and combinations thereof, wherein said allergen is applied to said solid phase as an allergen composition; said allergen composition being formed from combining an allergen with a pretreatment substance; wherein said pretreatment substance is selected from the group consisting of: denaturants excluding organic solvents and concentrated salt solutions; organic solvents; cross-linking agents; concentrated salt solutions; and combinations thereof containing, on the basis of allergen protein in a solvent, i) from 0.05 to 4.0 mg/mL of Altenaria allergen,
ii) from 0.05 to 50 mg/mL of Aspergillus allergen,
iii) from 0.8 to 81.6 mg/mL of Bermuda grass allergen,
iv) from 0.1 to 6.0 mg/mL of birch allergen,
v) from 0.6 to 20.6 mg/ml of cat allergen,
vi) from 0.04 to 4.5 mg/ml of mountain cedar allergen,
vii) from 0.1 to 20.5 mg/ml of Japanese cedar allergen,
viii) from 0.05 to 38.4 mg/ml of Cladosporium allergen,
ix) from 1.3 to 38.4 mg/ml of dog allergen,
x) from 0.7 to 22.4 mg/ml of D. farinase allergen,
xi) from 0.6 to 84.2 mg/ml of D. pteronyssinus allergen,
xii) from 0.1 to 146.0 mg/ml of elm allergen,
xiii) from 0.02 to 0.2 mg/ml of feather allergen,
xiv) from 0.2 to 148.2 mg/ml of giant ragweed allergen,
xv) from 0.4 to 100 mg/ml of house dust allergen,
xvi) from 0.05 to 21.8 mg/ml of June/Kentucky bluegrass allergen,
xvii) from 0.2 to 47.0 mg/ml of lamb's quarters allergen,
xviii) from 0.1 to 166.3 mg/ml of maple allergen,
xix) from 0.3 to 90.4 mg/ml of mugwort allergen,
xx) from 0.1 to 12 mg/ml of mulberry allergen,
xxi) from 0.2 to 29.2 mg/ml of oak allergen,
xxii) from 0.1 to 66.8 mg/ml of olive allergen,
xxiii) from 1.0 to 40.0 mg/ml of Parietaria allergen,
xxiv) from 1.7 to 130.4 mg/ml of plantain allergen,
xxv) from 0.1 to 4.8 mg/ml of Penicillium allergen,
xxvi) from 0.05 to 17.3 mg/ml of perennial rye allergen,
xxvii) from 0.2 to 151.6 mg/ml of short ragweed allergen, or
xxviii) from 0.05 to 6.6 mg/ml of timothy allergen, and b) contacting said test sample to said solid phase, thereby immobilizing allergen-speciffic IgE antibody from the test sample upon said solid phase by forming allergen/antibody complexes; and c) detecting said immobilized allergen-specific antibody to determine the presence or amount of the antibody in the test sample.

43. The method according to claim 42, wherein step c) comprises contacting said solid phase with an indicator reagent to determine the presence or amount of IgE in the test sample.

44. The method according to claim 43, wherein said indicator reagent comprises a label conjugated to a binding member specific for a member selected from the group consisting of allergen, IgE and an ancillary specific binding member.

45. The method according to claim 44, wherein said indicator reagent comprises a label conjugated to an anti-IgE antibody or anti-IgE antibody fragment.

46. The method according to claim 45, wherein free or bound labeled anti-IgE antibody is detected to determine the presence or amount of IgE in the test sample.

47. The method according to claim 44, wherein said label is a member selected from the group consisting of chromogens, catalysts, fluorescent compounds, chemiluminescent compounds, radioactive isotopes, colloidal metallic particles, colloidal selenium particles, dye particles, enzymes, substrates, organic polymer latex particles and liposomes or other vesicles containing signal producing components.

48. The method according to claim 43, further comprising the step of washing unbound indicator reagent from said solid phase prior to detecting the presence or amount of IgE in the test sample.

49. The method according to claim 42, wherein said solid phase is a member selected from the group consisting of cellulose, cellulose derivatives, silica, fiberglass, a porous polymer matrix, porous gels, polymeric films, agarose and porous fibrous matrixes.

50. A method for determining the presence or amount of IgE in a test sample, comprising the steps of:
a) providing at least one allergen immobilized upon a solid phase, wherein said solid phase comprises a material selected from the group consisting of nitrocellulose, nitrocellulose derivatives, nitrocellulose compounds, and combinations thereof, wherein said allergen is applied to said solid phase as an allergen composition comprising.:
  i) a solvent;
  ii) an allergen solubilized in said solvent, thereby forming an allergen solution; and
  iii) a pretreatment substance selected from the group consisting of: denaturants excluding organic solvents and concentrated salt solutions; organic solvents, crosslinking agents; concentrated salt solutions, and combinations thereof, wherein said allergen solution is combined with said pretreatment substance to form an allergen composition;
b) contacting the test sample to said solid phase, thereby immobilizing allergen-specific IgE antibody from the test sample upon said solid phase by forming allergen/antibody complexes; and
c) detecting said immobilized allergen-specific antibody to determine the presence or amount of the antibody in the test sample.

51. A kit for determining the presence or amount of IgE in a test sample, comprising:
a) an allergen immobilized upon a solid phase comprising a material selected from the group consisting of nitrocellulose, nitrocellulose derivatives, nitrocellulose compounds, and combinations thereof, wherein said allergen is applied to said solid phase as an allergen composition comprising:
  i) a solvent;
  ii) an allergen solubilized in said solvent, thereby forming an allergen solution; and
  iii) a pretreatment substance selected from the group consisting of: denaturants excluding organic solvents and concentrated salt solutions; organic solvents; crosslinking agents; concentrated salt solution,; and combinations thereof, wherein said allergen solution is combined with said pretreatment substance to form an allergen composition; and
b) an indicator reagent in a container, wherein said indicator reagent is used to determine the presence or amount of IgE in the test sample, wherein said indicator reagent comprises a label conjugated to a binding member specific for a member selected from the group consisting of the allergen, IgE and an ancillary specific binding member.

* * * * *